United States Patent [19]

Dörschug

[11] Patent Number: 5,656,722

[45] Date of Patent: Aug. 12, 1997

[54] $A^{21}$-, $B^{30}$ - MODIFIED INSULIN DERIVATIVES HAVING AN ALTERED ACTION PROFILE

[75] Inventor: Michael Dörschug, Bochum, Germany

[73] Assignee: Hoechst Aktiengesellschaft, Frankfurt am Main, Germany

[21] Appl. No.: 304,593

[22] Filed: Sep. 12, 1994

Related U.S. Application Data

[63] Continuation of Ser. No. 46,481, Apr. 9, 1993, abandoned, which is a continuation of Ser. No. 929,510, Aug. 19, 1992, abandoned, which is a continuation of Ser. No. 431,844, Nov. 6, 1989, abandoned.

[30] Foreign Application Priority Data

Nov. 8, 1988 [DE] Germany .................. 38 37 825.6

[51] Int. Cl.$^6$ .................................................. A61K 38/28
[52] U.S. Cl. .................................... 530/303; 530/304
[58] Field of Search .......................... 530/303, 304; 514/3, 12

[56] References Cited

U.S. PATENT DOCUMENTS 4,701,440  10/1987  Grau ........................................ 514/3

FOREIGN PATENT DOCUMENTS

| | | |
|---|---|---|
| 62066/86 | 5/1986 | Australia . |
| 75916/87 | 1/1988 | Australia . |
| 13976/88 | 9/1988 | Australia . |
| 0046979 | 8/1981 | European Pat. Off. . |
| 0133285 | 2/1985 | European Pat. Off. ......... 495/351 |
| 0214826 | 3/1987 | European Pat. Off. . |
| 0254516 | 6/1987 | European Pat. Off. . |

OTHER PUBLICATIONS

Schome et al. Diabetes vol. 27 (1978) 8–15.
Geigee, Chem–Zeitung vol. 100 No. 3 pp. 54–56 (Jan. 1976).
Thompson et al Int'l J. Pept. Prot. Res. vol. 23 (1984) 394–401.
Schwartz et al PNAS vol. 84 pp. 6408–6411 (Sep. 1987).
Volund Diabetic Medicine 8, 839, 1991.
Neubauer, "The Immunogenicity of Different Insulins in Several Animal Species", Diabetes, vol. 27, No. 1 (1977).
"Galenics Of Insulin, The Physico–chemical and Pharmaceutical Aspects of Insulin and Insulin Preparations", J. BRANGE: Springer–Verlag Berlin Heidelberg 1987, pp. 35–36.
Markussen et al., Soluble, prolonged–acting insulin derivatives, II. Degree of protraction and crystallizability of insulins substituted in positions A17, B8, B13, B27 and B30, Protein Engineering 1(3):215–223 (1987).
Markussen et al., Soluble, prolonged–acting insulin derivatives, III. Degree of protraction, crystallizability and chemical stability of insulins substituted in positions A21, B13, B23, B27, and B30, Protein Engineering 2(2):157–166 (1988).
Zinman, Bernard, The Physiologic Replacement of Insulin, Medical Intelligence, vol. 32, No. 6, pp. 363–370 (1989).
Sundby, F., Separation and Characterization of Acid–induced Insulin Transformation Products by Paper Electrophoresis in 7 M Urea, The Journal of Biological Chemistry, vol. 237, No. 11, pp. 3406–3411 (1962).
Burgermeister, W., et al., The Isolation of Insulin from the Pancreas, Reprint from the Handbook of Experimental Pharmacology, pp. 715–727 (1975) Insulin Humanum, European Pharmacopeia 838 (1993).

*Primary Examiner*—David Lukton
*Attorney, Agent, or Firm*—Finnegan, Henderson, Farabow, Garrett & Dunner, L.L.P.

[57] ABSTRACT

New insulin derivatives, the use thereof, and a pharmaceutical composition containing them Insulin derivatives having an isoelectric point between 5 and 8.5, or physiologically tolerated salts thereof, of the Formula II

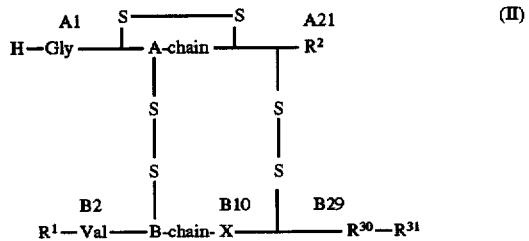

in which:

$R^1$ at position B1 denotes H or H-Phe;

$R^2$ at position A21 denotes a genetically encodable L-amino acid selected from the group consisting of Gly, Ala, Val, Leu, Ile, Pro, Phe, Trp, Met, Ser, Thr, Cys, Tyr, Asp, and Glu;

$R^{30}$ represents the residue of a neutral genetically encodable L-amino acid selected from the group consisting of Ala, Thr, and Ser;

$R^{31}$ represents 1, 2, or 3 neutral or basic alpha amino acids, wherein at least one of the alpha amino acids is selected from the group consisting of Arg, Lys, Hyl, Orn, Cit, and His;

X represents His at position B10; and the sequences A1 to A20 and B1 to B29 in Formula II correspond to a mammalian insulin;

excluding those insulin derivatives in which simultaneously:
$R^1$ at position B1 denotes Phe; and
$R^3$ is one alpha amino acid having a terminal carboxyl group.

15 Claims, No Drawings

$A^{21}$-, $B^{30}$ - MODIFIED INSULIN DERIVATIVES HAVING AN ALTERED ACTION PROFILE

This application is a continuation, of application Ser. No. 08/046,481 filed Apr. 9, 1993, abandoned, which is a continuation of application Ser. No. 07/929,510, filed Aug. 19, 1992, abandoned, which is a continuation of application Ser. No. 07/431,844, filed Nov. 6, 1989, now abandoned.

BACKGROUND OF THE INVENTION

As is known, insulin and insulin derivatives are required in considerable quantities for the treatment of the disease diabetes mellitus, and some of them are also produced on an industrial scale. Despite the considerable number of insulin compositions and modifications with different action profiles which are already in existence, there is still a need, because of the variety of organisms with their inter- and intraindividual variations, for other insulin products which in turn have other properties and action characteristics.

Insulin derivatives with a delayed action are described, for example, in EP-B 132,769 and EP-B 132,770. These are specifically derivatives with a basic modification in position B31 of the insulin B chain, of the following formula I:

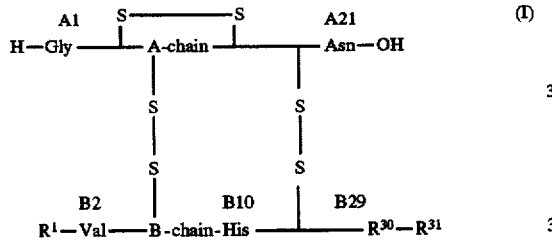

in which $R^1$ denotes H or H-Phe, $R^{30}$ represents the residue of a neutral, genetically encodable L-amino acid, and $R^{31}$ represents a physiologically acceptable organic group which is basic in nature and has up to 50 carbon atoms, in whose structure 0 to 3 α-amino acids are involved and whose terminal carboxyl group which is present where appropriate can be free, in the form of an ester functionality, an amide functionality, a lactone or reduced to $CH_2OH$.

Characteristic of these insulin derivatives is an isoelectric point between 5.8 and 8.5 (measured by isoelectric focusing). The fact that the isoelectric point is shifted from the isoelectric point of unmodified natural insulin or proinsulin (at pH=5.4) into the neutral range derives from the additional positive charge(s) located on the surface of the molecule as a result of the basic modification. This makes these insulin derivatives with a basic modification less soluble in the neutral range than, say, natural insulin or proinsulin, which are normally dissolved in the neutral range.

The delaying or depot action of the insulin derivatives with a basic modification, of the formula I, derives from their sparing solubility at the isoelectric point. According to the two abovementioned publications, the redissolution of the insulin derivatives under physiological conditions is achieved by elimination of the additional basic groups, which is brought about, depending on the derivative, by trypsin or trypsin-like and/or carboxypeptidase B or carboxypeptidase B-like and/or esterase activity. The eliminated groups are in each case either purely physiological metabolites or else easily metabolized physiologically acceptable substances.

The abovementioned depot principle resulting from basic modification of the insulin has also been further utilized by the provision and corresponding use of other insulin derivatives with basic modifications, mainly within the A and B chains; cf. for example EP-A 0,194,864 and EP-A 0,254,516.

In the insulin derivatives specified in EP-A 0,194,864, a basic amino acid is incorporated in the B27 position and/or a neutral amino acid is located at positions A4, A17, B13 and/or B21; in addition, the C-terminal carboxyl group of the B chain is blocked by an amide or ester residue.

The insulin derivatives specified in EP-A 0,254,516 are very similar to those specified in the abovementioned EP-A; however, in this case, with the aim of increasing the stability of the relevant pharmaceutical compositions at the weakly acid pH values, the amino acid Ash in position A21 can also be replaced by other amino acids which are more stable in acid medium, such as, for example, Asp. As is known, Ash (=asparagine) differs from Asp (=aspartic acid) by the blocking of one of the two carboxyl groups by the amide group:

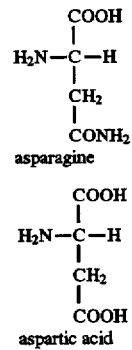

Rapid-acting insulin derivatives are said to result from yet another modification of the insulin molecule in the A and B chain, in particular by replacing the amino acid His, which is responsible for the formation of a complex with zinc—and thus for a certain delaying action, in the B10 position by other appropriate amino acids; cf. EP-A 0,214,826.

All the insulin derivatives specified in the 3 lastmentioned publications are mainly modified within the A and B chains; they are prepared by genetic engineering routes.

SUMMARY OF THE INVENTION

In the attempt to increase the stability in acid medium of the insulin derivatives with a basic modification on the C-terminal end of the B chain as specified in the European Patents EP-B 0,132,769 and EP-B 0,132,770 mentioned in the introduction, and, where appropriate, also to alter the action profile thereof, it has now been found that this object is achieved in an advantageous manner by replacing $Asn^{A21}$ by other genetically encodable amino acids which contain no amide group and, where appropriate, by replacing $His^{B10}$ by other genetically encodable amino acids.

DESCRIPTION OF THE PREFERRED EMBODIMENTS

Hence the invention relates to insulin derivatives of the formula II

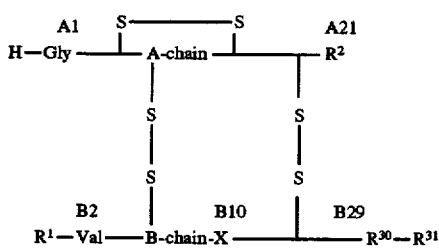

in which:

$R^1$ denotes H or H-Phe, $R^2$ denotes a genetically encodable L-amino acid which contains no amide group, $R^{30}$ represents the residue of a neutral genetically encodable L-amino acid, $R^{31}$ represents a physiologically acceptable organic group which is basic in nature and has up to 50 carbon atoms, in whose structure 0 to 3 α-amino acids are involved and whose terminal carboxyl group which is present where appropriate can be free, in the form of an ester functionality, an amide functionality, a lactone or reduced to $CH_2OH$, and X represents a genetically encodable L-amino acid, having an isoelectric point between 5 and 8.5, and the physiologically tolerated salts thereof.

The new insulin derivatives and the physiologically tolerated salts thereof are stable at the weakly acid pH values of appropriate pharmaceutical compositions even for extended periods and have—especially when $His^{B10}$ has also been replaced by other amino acids—an altered (shorter) action profile compared with the known—unaltered—insulin derivatives with a basic modification of the formula I indicated in the introduction.

$R^1$ in formula II is preferably H-Phe.

Genetically encodable L-amino acids containing no amide group—for $R^2$—are Gly, Ala, Ser, Thr, Val, Leu, Ile, Asp, Glu, Cys, Met, Arg, Lys, His, Tyr, Phe, Trp, Pro;

Gly, Ala, Ser, Thr, Asp and Glu are preferred, especially Asp.

Neutral genetically encodable L-amino acids—for $R^{30}$—are Gly, Ala, Ser, Thr, Val, Leu, Ile, Ash, Gln, Cys, Met, Tyr, Phe and Pro; Ala, Thr and Ser are preferred.

$R^{31}$ is a physiologically acceptable organic group which is basic in nature and has up to 50 carbon atoms and in whose structure 0–3 α-amino acids are involved. When no α-amino acids are involved in the structure of $R^{31}$, examples of suitable basic groups for this residue are the following:

amino-$(C_2-C_6)$-alkoxy, $(C_1-C_4)$-alkylamino-$(C_2-C_6)$-alkoxy, di-$(C_1-C_4)$-alkylamino-$(C_2-C_6)$-alkoxy, tri-$(C_1-C_4)$ammonio-$(C_2-C_6)$-alkoxy, amino-$(C_2-C_6)$-alkylamino, [$(C_1-C_4)$-alkyl-amino]- $(C_2-C_6)$-alkylamino, di-$(C_1-C_4)$-alkylamino-$(C_2-C_6)$-alkylamino or [tri-$(C_1-C_4)$-alkylamino]-$(C_2-C_6)$-alkylamino, especially —O—[$CH_2$]—$NR_2$ and —O—[$CH_2$]—$N^{30}R_3$, —NH—[$CH_2$]$_p$—$NR_2$ or —NH—[$CH_2$]$_p$—$^+R_3$, in which p is 2 to 6, and R is identical or different and represents hydrogen or $(C_1-C_4)$-alkyl.

When up to 3 α-amino acids are involved in the structure of $R^{31}$, these are primarily neutral or basic naturally occurring L-amino acids and/or the D-amino acids corresponding thereto. Neutral naturally occurring amino acids are, in particular, Gly, Ala, Ser, Thr, Val, Leu, Ile, Ash, Gln, Cys, Met, Tyr, Phe, Pro and Hyp. Basic naturally occurring amino acids are, in particular, Arg, Lys, Hyl, Orn, Cit and His. If only neutral α-amino acids are involved, the terminal carboxyl group thereof cannot be free—in order for $R^{31}$ to be basic in nature; on the contrary, the carboxyl group must in this case be amidated or esterified with a basic group, suitable basic groups for this being, for example, the abovementioned basic groups—in the case where no α-amino acids are involved in the structure of $R^{31}$. Of course, these basic ester or amide groups can also block the carboxyl group of basic α-amino acids. Also possible and suitable for blocking the carboxyl group of the basic α-amino acids are—if the blocking is desired—neutral ester or amide groups such as, for example, $(C_1-C_6)$-alkoxy, $(C_3-C_6)$-cycloalkyloxy, $NH_2$, $(C_1-C_6)$-alkylamino or di-$(C_1-C_6)$-alkylamino.

Of course, the terminal carboxyl group can be in the form of a lactone only if the terminal amino acid is a hydroxyamino acid.

Moreover, the terminal carboxyl group can also be reduced to $CH_2OH$.

$R^{31}$ is preferably composed of 1, 2 or 3 of the abovementioned basic naturally occurring amino acids; $R^{31}$ is particularly preferably Arg-OH or Arg-Arg-OH.

Suitable genetically encodable L-amino acids—for X—are the same amino acids as for $R^2$, but the genetically encodable L-amino acids which contain an amide group—which are Ash and Gln—are also possible in this case; the latter—Asn and Gln—are in fact preferred in this case. If Asn or Gln is located in position B10, the amide group is at least stable in weakly acid medium (in contrast to Asn or Gln in position A21). The sequences (A1–A20) and (B1–B9, B11–B29) are preferably the sequences of human, porcine or bovine insulin, especially the sequences of human insulin.

Examples of insulin derivatives of the formula II are:

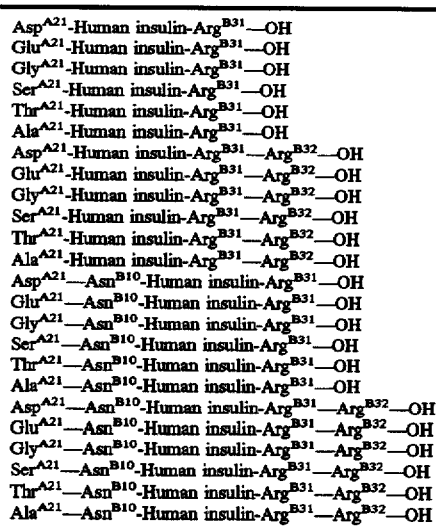

The insulin derivatives of the formula II are prepared mainly by a genetic manipulation by means of site-directed mutagenesis using standard methods.

For this purpose, a gene structure coding for the desired insulin derivative of the formula II is constructed and its expression is brought about in a host cell—preferably in a bacterium such as E. coli or a yeast, in particular Saccharomyces cerevisiae—and—if the gene structure codes for a fusion protein—the insulinderivative of the formula II is liberated from the fusion protein; analogous methods are described, for example, in EP-A 0,211,299, EP-A 0,227,938, EP-A 0,229,998, EP-A 0,286,956 and German Patent Application P 38 21 159.9 dated Jun. 23, 1988 (HOE 88/F 158).

After cell disruption, the fusion protein portion is eliminated either chemically using cyanogen halide—cf. EP-A 0,180,920 or enzymatically using lysostaphin—cf. DE-A 3,739,347.

The insulin precursor is then subjected to oxidative sulfitolysis by the method described, for example, by R. C. Marshall and A. S. Inglis in "Practical Protein Chemistry—A Handbook" (edited by A. Darbre) 1986, pages 49–53, and subsequently renatured in the presence of a thiol with the formation of the correct disulfide bridges, for example by the method described by G. H. Dixon and A. C. Wardlow in Nature (1960), pages 721–724.

The C peptide is removed by cleavage with trypsin—for example by the method of Kemmler et al., J. B. C. (1971), pages 6786–6791, and the insulin derivative of the formula II is purified by known techniques such as chromatography—cf., for example, EP-A-0,305,760—and crystallization.

The insulin derivatives of the formula II with $R^2$=Asp and X=His are expediently prepared by hydrolysis of the known insulin derivatives which have a basic modification and the formula I in aqueous acidic medium (because only the amide group of the asparagine in position A21 must be hydrolyzed in this case), preferably at pH values between about 2 and about 4, in particular of about 2.5, and at temperatures of about 0° to about 40° C., preferably at room temperature.

The insulin derivatives of the formula II, according to the invention, and/or the physiologically tolerated salts thereof (such as, for example, the alkali metal or ammonium salts) are mainly used as active substances for a pharmaceutical composition for the treatment of diabetes mellitus.

The pharmaceutical composition is preferably a solution or suspension for injection; it contains at least one insulin derivative of the formula II and/or at least one of the physiologically tolerated salts thereof in dissolved, amorphous and/or crystalline—preferably in dissolved—form.

The composition preferably has a pH between about 2.5 and 8.5, in particular between about 4.0 and 8.5, and contains a suitable tonicity agent, a suitable preservative and, where appropriate, a suitable buffer, as well preferably a certain zinc ion concentration, all, of course, in sterile aqueous solution. All the ingredients of the composition apart from the active substance form the composition vehicle.

Examples of suitable tonicity agents are glycerol, glucose, mannitol, NACl, and calcium or magnesium compounds such as $CaCl_2$, $MgCl_2$ etc.

The choice of the tonicity agent and/or preservative influences the solubility of the insulin derivative or the physiologically tolerated salt thereof at the weakly acid pH values.

Examples of suitable preservatives are phenol, m-cresol, benzyl alcohol and/or p-hydroxybenzoic esters.

Examples of buffer substances which can be used, in particular for adjusting a pH between about 4.0 and 8.5, are sodium acetate, sodium citrate, sodium phosphate etc. Otherwise, also suitable for adjusting the pH are physiologically acceptable dilute acids (typically HCl) or alkalis (typically NaOH).

When the composition contains zinc a content of 1 µg to 2 mg, in particular from 5 µg to 200 µg, of zinc/ml is preferred.

In order to vary the action profile of the composition according to the invention it is also possible to admix unmodified insulin, preferably bovine, porcine or human insulin, in particular human insulin.

Preferred concentrations of active substance are those corresponding to about 1–1500, also preferably about 5–1000, and in particular about 40–400, international units/ml.

The invention is now explained in detail by the examples which follow.

A) Preparation By Genetic Manipulation

EXAMPLE 1

Construction of a plasmid for the preparation of Gly (A21)-human insulin Arg (B31-OH)

The plasmid pSW3 has been described in German Patent Application P 38 21 159.9 (HOE 88/F 158). The plasmid DNA is reacted with the restriction enzymes PvuII and SalI and subsequently treated with bovine alkaline phosphatase. The two resulting fragments are separated by gel electrophoresis, and the large fragment is isolated. This fragment is linked in a T4 DNA ligase reaction with the following synthetic DNA sequence:

```
5'- CTG GAA AAC TAC TGT GGT TGA TAG
    GAC CTT TTG ATG ACA CCA ACT ATC AGCT - 5'
```

Competent E. coli W3110 cells are transformed with the ligation mixture. The transformation mixture is plated out on NA plates which contain 20 µg of Ap (=Ampicillin)/ml and incubated at 37° C. overnight. An overnight culture is obtained from single colonies, and plasmid DNA is obtained from this. This DNA is characterized by means of restriction analysis and DNA sequence analysis. Correct plasmids which encode the modified A chain are called pIK100. Expression is carried out in analogy to Example 3 of the abovementioned German Patent Application P 38 21 159.9. The modified mono-Arg-insulin is likewise prepared in analogy to the preparation of the unmodified mono-Arg-insulin described in this German Patent Application.

EXAMPLE 2

Construction of a plasmid for the preparation of Ser (A21)- human insulin (Arg B31-OH)

The construction corresponds to the route described in the above example. The synthetic DNA sequence is, however, modified as follows:

```
5'- CTG GAA AAC TAC TGT TCA TGA TAG
    GAC CTT TTG ATG ACA AGT ACT ATC AGCT - 5'
```

The plasmid pIK110 which has an additional BspHI recognition sequence is obtained.

EXAMPLE 3

Construction of a plasmid for the preparation of Gly (A21)- Asn(B10)-human insulin Arg(B31-OH)

DNA from the plasmid pIK100 is cleaved with the restriction enzymes HpaI and DraIII and treated with bovine alkaline phosphatase. The two resulting fragments are separated by gel electrophoresis, and the larger of the two fragments is isolated. The fragment is ligated with the synthetic DNA sequence

```
5'- AAC CAA CAC TTG TGT GGT TCT AAC TTG
    TTG GTT GTG AAC ACA CCA AGA TTG      - 5'
``` and competent E. coli W3110 cells are transformed with the ligation mixture. Further characterization of the resulting plasmid pIK101 is carried out as described in Example 1.

EXAMPLE 4

Construction of a plasmid for the preparation of Ser (A21)- Asn(B10)-human insulin The construction corresponds to the cloning described in Example 3, but starting from DNA from the plasmid pIK110. The newly constructed plasmid is called pIK111.

EXAMPLE 5

Construction of an expression plasmid for monkey proinsulin

Monkey proinsulin differs from human proinsulin merely by replacement of a single amino acid in the C peptide (B37-Pro in place of Leu in this position of human proinsulin).

The plasmid pSW3 is opened with HpaI and SalI and the remaining plasmid DNA is isolated. The DraIII-SalI monkey proinsulin fragment is isolated from the plasmid pK50 described in EP-A0.229.998. The two fragments are linked to the synthetic DNA fragment

```
5' - AAC CAG CAC CTG TGC GGT TCT CAC CTA
     TTG GTC GTG GAC ACG CCA AGA GTG       - 5'
``` in a T4 DNA ligase reaction. The plasmid pSW2 is obtained, and its DNA is used hereinafter as starting material for the constructions of the expression plasmids encoding the di-Arg-human insulin derivatives.

EXAMPLE 6

Construction of a plasmid for the preparation of Gly(A21)-human insulin Arg(B31)-Arg(B32)-OH DNA of the plasmid pSW2 is cleaved with PvuII and SalI in accordance with Example 1 and ligated with the synthetic DNA from Example 1; the result is the plasmid pSW21.

EXAMPLE 7

Construction of a plasmid for the preparation of Ser(A21)-human insulin-Arg(B31)-Arg(B32)-OH The plasmid pSW22 is constructed starting from pSW2 DNA in analogy to Example 2.

EXAMPLE 8

Construction of a plasmid for the preparation of Gly(A21)-Asn(B10)-human insulin-Arg(B31)-Arg(B32)-OH The plasmid pSW23 is constructed starting from pSW21 DNA in analogy to Example 3.

The following sequence is used as synthetic DNA sequence for this:

```
5' - AAC CAA CAC TTG TGT GGT TCT AAC CTA
     TTG GTT GTG AAC ACA CAA AGA TTG -5'
```

EXAMPLE 9

Construction of a plasmid for the preparation of Set(A21)-Asn(B10)-human insulin-B31(Arg)-B32(Arg)-OH The plasmid pSW24 is constructed starting from pSW22 DNA in analogy to Example 4 using the synthetic DNA sequence described in Example 8.

B) Preparation of $Asp^{A21}$-Human Insulin-$Arg^{B31}$-$Arg^{B32}$-OH From Human Insulin-$Arg^{B31}$-$Arg^{B32}$-OH by Hydrolysis 1 g of human insulin-$Arg^{31}$-$Arg^{32}$-OH is suspended in 100 ml of $H_2O$. The pH is adjusted to 2.5 by addition of HCl, and the solution is left at 37° C. After one week about one half of the material has been converted into $Asp^{A21}$-human insulin-$Arg^{B31}Arg^{B32}$-OH. The product is separated from the starting material in a manner known per se on an anion exchanger, is precipitated from the eluate and is crystallized in a buffer which contains 10.5 g of citric acid, 1 g of phenol and 5 ml of a 1% strength zinc chloride solution per liter with a protein concentration of 5 g/l at pH 6.0. The yield is 390 mg of $Asp^{A21}$-human insulin-$Arg^{B31}$-$Arg^{B32}$.

C) Preparation of an Injection Solution

The insulin derivative from B is dissolved at a concentration of 1.4 mg/ml in a sterile vehicle solution of the following composition (per ml):

18 mg of glycerol, 10 mg of benzyl alcohol, 80 μg of $Zn^{2+}$, pH 4.0.

D) Action Profile of an $Asp^{A21}$-Human Insulin-$Arg^{B31}$-$Arg^{B32}$-OH Composition in dogs by comparison with human insulin-$Arg^{B31}$-$Arg^{B32}$-OH and basal H insulin Hoechst$^{(R)}$= an NPH (neutral protamine Hagedorn) composition containing about 10 μg of $Zn^{2+}$.

| Product | | Blood glucose as a % of the initial level in hours (h) | | | | |
|---|---|---|---|---|---|---|
| | | 1 h | 2 h | 3 h | 5 h | 7 h |
| According to the invention | $Asp^{A21}$-human insulin $Arg^{B31}$—$Arg^{B32}$—OH | 99 | 62 | 51 | 75 | 98 |
| Comparison | Human insulin $Arg^{B31}$—$Arg^{B32}$—OH | 77 | 52 | 64 | 85 | 98 |
| | Basal H insulin Hoechst$^{(R)}$ | 71 | 49 | 59 | 83 | 100 |

This example shows that $Asp^{A21}$-human insulin-$Arg^{B31}$-$Arg^{B32}$-OH has the same advantageous basal profile as human insulin-$Arg^{B31}$-$Arg^{B32}$-OH. In addition, $Asp^{A21}$-human-insulin-$Arg^{B31}$-$Arg^{B32}$-OH has the advantageous property that the compound is stable for a long time under the chosen conditions.

I claim:

1. An insulin derivative having an isoelectric point between 5 and 8.5, or a physiologically tolerated salt thereof, of the Formula II in which:

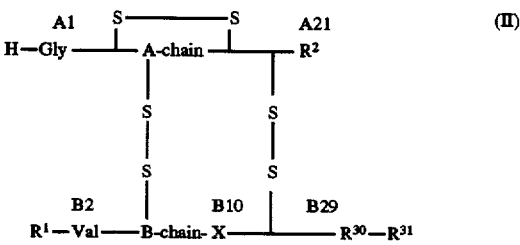

R$^1$ at position B1 denotes H or H-Phe;

R$^2$ at position A21 denotes a genetically encodable L-amino acid selected from the group consisting of Gly, Ala, Val, Leu, Ile, Pro, Phe, Trp, Met, Ser, Thr, Cys, Tyr, Asp, and Glu;

R$^{30}$ represents the residue of a neutral genetically encodable L-amino acid selected from the group consisting of Ala, Thr, and Ser;

R$^{31}$ represents 1, 2, or 3 neutral or basic α-amino acids, wherein at least one of the α-amino acids is selected from the group consisting of Arg, Lys, Hyl, Orn, Cit, and His;

X represents His at position B10; and the sequences A1 to A20 and B1 to B29 in Formula II correspond to a mammalian insulin;

excluding those insulin derivatives in which simultaneously:

$R^1$ at position B1 denotes Phe; and $R^{31}$ is one alpha amino acid having a terminal carboxyl group.

2. An insulin derivative or the physiologically tolerated salts thereof as claimed in claim 1, wherein $R^1$ in formula II represents H-Phe.

3. An insulin derivative or the physiologically tolerated salts thereof as claimed in claim 1, wherein $R^2$ in formula II represents Gly, Ala, Ser, Thr, Asp, or Glu.

4. An insulin derivative or the physiologically tolerated salts thereof as claimed in claim 1, wherein $R^{31}$ in formula II represents Arg-Arg-OH.

5. An insulin derivative or the physiologically tolerated salts thereof as claimed in claim 1, wherein the sequences (A1 to A20) and (B1 to B29) in formula II are the sequences of human, porcine, or bovine insulin.

6. A pharmaceutical composition that contains an effective amount of at least one insulin derivative of the formula II, or at least one of the physiologically tolerated salts thereof, as claimed in claim 1, in dissolved, amorphous or crystalline form for the treatment of diabetes.

7. A pharmaceutical composition as claimed in claim 6, which additionally contains 1 µg to 2 mg of zinc/ml.

8. A pharmaceutical composition as claimed in claim 6, which additionally contains unmodified insulin.

9. A method for treating a patient suffering from diabetes mellitus, which comprises administering to said patient a pharmaceutical composition as claimed in claim 6.

10. An insulin derivative or the physiologically tolerated salts thereof as claimed in claim 3, wherein $R^2$ in formula II represents Asp.

11. An insulin derivative or the physiologically tolerated salts thereof as claimed in claim 5, wherein the sequences (A1 to A20) and (B1 to B29) in formula II are the sequences of human insulin.

12. A pharmaceutical composition that contains an effective amount of at least one insulin derivative of the formula II, or at least one of the physiologically tolerated salts thereof, as claimed in claim 8, in dissolved form for the treatment of diabetes.

13. A pharmaceutical composition as claimed in claim 7, which additionally contains 5 µg to 200 µg of zinc/ml.

14. A pharmaceutical composition as claimed in claim 8, wherein said unmodified insulin is unmodified human insulin.

15. An insulin derivative or the physiologically tolerated salts thereof as claimed in claim 5, wherein $R^1$ represents H-Phe, $R^2$ represents Gly, $R^{30}$ represents Thr, and $R^{31}$ represents Arg-Arg-OH.

* * * * *